United States Patent
Oishi (10) Patent No.: US 9,519,980 B2
(45) Date of Patent: Dec. 13, 2016

(54) OBJECT INFORMATION ACQUIRING APPARATUS

(71) Applicant: CANON KABUSHIKI KAISHA, Tokyo (JP)

(72) Inventor: Takuji Oishi, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/711,920

(22) Filed: May 14, 2015

(65) Prior Publication Data

US 2015/0339814 A1    Nov. 26, 2015

(30) Foreign Application Priority Data

May 26, 2014 (JP) .................. 2014-108040

(51) Int. Cl.
  *G06K 9/00* (2006.01)
  *G06T 11/00* (2006.01)
  *A61B 5/00* (2006.01)
  *A61B 5/145* (2006.01)

(52) U.S. Cl.
  CPC .......... *G06T 11/008* (2013.01); *A61B 5/0095* (2013.01); *G06T 11/00* (2013.01); *A61B 5/14542* (2013.01); *G06T 2207/10024* (2013.01); *G06T 2207/10084* (2013.01); *G06T 2207/30104* (2013.01)

(58) Field of Classification Search
  CPC .......... G06T 2207/10084; G06T 2207/10024; G06T 11/008; G06T 7/0012; G06T 2211/40
  USPC .................. 382/128, 131
  See application file for complete search history.

(56) References Cited

U.S. PATENT DOCUMENTS

| | | | |
|---|---|---|---|
| 5,582,173 A * | 12/1996 | Li .............. | G01S 7/52034 128/916 |
| 6,205,350 B1 | 3/2001 | Lorenz et al. ....... | 600/425 |
| 6,567,406 B1 * | 5/2003 | Skemer ........... | H04L 12/2856 370/392 |
| 7,274,810 B2 * | 9/2007 | Reeves ........... | G06T 7/0012 382/128 |
| 7,525,661 B2 * | 4/2009 | Mandelis .......... | G01B 21/085 356/237.1 |
| 7,672,424 B2 * | 3/2010 | Ziegler ........... | G06T 11/006 378/19 |
| 7,860,283 B2 * | 12/2010 | Begelman ........ | A61B 5/02007 345/418 |

(Continued)

*Primary Examiner* — Tom Y Lu
(74) *Attorney, Agent, or Firm* — Fitzpatrick, Cella, Harper & Scinto (57) ABSTRACT

An object information acquiring apparatus is used that has a receiver receiving acoustic waves propagating through an object at a plurality of measurement positions; and a processor acquiring on a two-dimensional flat surface projection image data obtained by projecting a distribution of property information relating to a measurement target within the object, wherein the processor acquires intensity-dependent three-dimensional image data within the object and non-intensity-dependent three-dimensional image data within the object, based on the acoustic waves, determines voxel coordinates projected onto the two-dimensional flat surface, based on the intensity-dependent three-dimensional image data, and acquires the projection image data, based on values of the non-intensity-dependent three-dimensional image data.

32 Claims, 8 Drawing Sheets

(56) References Cited

U.S. PATENT DOCUMENTS

| | | | | |
|---|---|---|---|---|
| 8,582,856 B2* | 11/2013 | Endo | ................. | G06T 7/0012 |
| | | | | 345/420 |
| 8,687,868 B2* | 4/2014 | Fukutani | ............ | A61B 5/0073 |
| | | | | 367/7 |
| 8,920,321 B2* | 12/2014 | Yoda | ............... | G01N 29/2418 |
| | | | | 600/437 |
| 2008/0285048 A1* | 11/2008 | Chen | ............... | G01B 11/2441 |
| | | | | 356/492 |
| 2010/0331662 A1* | 12/2010 | Fukutani | ............ | A61B 5/0059 |
| | | | | 600/407 |

* cited by examiner

OBJECT INFORMATION ACQUIRING APPARATUS

BACKGROUND OF THE INVENTION

Field of the Invention

The present invention relates to an object information acquiring apparatus.

Description of the Related Art

The development of photoacoustic tomography (PAT) systems, in which information on body functions is obtained using light and ultrasonic waves, has proceeded in the field of health care in recent years for use as apparatuses that enable non-invasive imaging of the interior of the body.

Photoacoustic tomography refers to a technology for acquiring images of internal tissue serving as a generation source of acoustic waves by using photoacoustic effects in which pulsed light generated from a light source is irradiated onto an object and acoustic waves (and typically, ultrasonic waves) are generated by absorption of light that has propagated and diffused within the object. Changes in the received acoustic waves over time are detected at a plurality of locations, and the resulting signals are subjected to mathematical analysis processing, namely reconfiguration, thereby enabling information relating to optical properties, such as the absorption coefficient within the object, to be visualized three-dimensionally.

For example, in the case of using near infrared light for the pulsed light, since near infrared light easily passes through water that composes a major portion of the body, it has the property of being easily absorbed by hemoglobin present in blood. Consequently, images of blood vessels can be obtained by visualizing absorption coefficients calculated based on acoustic waves generated by near infrared light. As a result, this technology is expected to be used to acquire images of and detect neovascularization frequently present around tumors.

Moreover, by comparing and arithmetically processing images of blood vessels obtained with pulsed light of different wavelengths, the ratio of oxyhemoglobin to total hemoglobin in blood, namely oxygen saturation, can be measured. Since blood surrounding malignant tumors is thought to have lower oxygen saturation than blood surrounding benign tumors, determination of oxygen saturation is expected to make it possible to distinguish between malignant and benign tumors. In addition, by selecting a suitable wavelength of pulse light, the presence ratios of substances composing an object can be determined using the same principle.

In addition, ultrasound examination apparatuses are apparatuses that convert information on body functions to images by receiving acoustic waves in the same manner as photoacoustic tomography. Ultrasound examination apparatuses acquire images by transmitting acoustic waves to the body and receiving acoustic waves that have been reflected in the body. Acoustic waves have the property of being reflected at an interface that has different acoustic impedance defined as the product of the propagation speed and density of the acoustic waves, and ultrasound examination apparatuses enable visualization of the distribution of acoustic impedance in the body.

In addition, when measuring an object in which there is movement such as blood flow, analyzing the frequency of the reflected waves makes it possible to determine the flow rate and direction thereof. Since this technique is referred to as the color Doppler method, the resulting flow rate and direction are referred to as color Doppler information.

A technique in which three-dimensional data is projected onto a two-dimensional flat surface is used as a method for displaying three-dimensional data obtained with an apparatus on a two-dimensional display. For example, an example of that technique is maximum intensity projection (MIP), in which the maximum value of voxels on the axis in the projecting direction is displayed on the projection plane. In the case of an object having a three-dimensionally complex shape as represented by blood vessels, although it is difficult to ascertain the overall structure if only a certain cross-section is displayed, displaying by MIP makes it easier to interpret three-dimensional shapes of blood vessels on a two-dimensional display.

In U.S. Pat. No. 6,205,350, a second set of three-dimensional data, for which structural information has been enhanced, is acquired from a first set of three-dimensional data obtained by measurement. The second set of three-dimensional data is projected onto a two-dimensional flat surface using voxels of the first set of three-dimensional data at the same coordinates as the contributing voxels when projected on a two-dimensional flat surface.

Patent Literature 1: U.S. Pat. No. 6,205,350

SUMMARY OF THE INVENTION

However, whether it be a region where a measurement target is present or a region in which it is not present, in the case of converting three-dimensional data obtained from similar values (non-intensity-dependent three-dimensional image data) to a first set of three-dimensional data, since this three-dimensional contains hardly any structural information, two-dimensional data also does not reflect the structure of the measurement target. As a result, there is the possibility of undesirable voxels not contributing to diagnosis being projected.

Three-dimensional image data, in which a measurement target and noise can typically be distinguished on the basis of voxel values (pixel value intensity) provided the signal/noise ratio (S/N ratio) is adequate for measurement, is referred to as "intensity-dependent three-dimensional image data". On the other hand, three-dimensional image data, in which theoretically the value of a measurement target and the value of a noise component are roughly the same and cannot be distinguished on the basis of voxel values (pixel value intensity) even if the S/N ratio is adequate for measurement, is referred to as "non-intensity-dependent three-dimensional image data". Furthermore, intensity-dependent three-dimensional image data can be said to be data for which structural information on an object is not lost as compared with non-intensity-dependent three-dimensional image data.

As has been described above, it was difficult to acquire projected images obtained by reflecting the value of a desired voxel of non-intensity-dependent three-dimensional image data.

The present invention is based on an awareness of such problems. An object of the present invention is to acquire image data projected onto a two-dimensional flat surface by selecting a desired voxel from non-intensity-dependent three-dimensional image data.

The present invention provides an object information acquiring apparatus, comprising:

a receiver that receives acoustic waves propagating through an object at a plurality of measurement positions; and a processor that acquires projection image data obtained by projecting on a two-dimensional flat surface a distribution of property information relating to a measurement target within the object, wherein
the processor
acquires intensity-dependent three-dimensional image data within the object and non-intensity-dependent three-dimensional image data within the object, based on the acoustic waves,
determines voxel coordinates projected onto the two-dimensional flat surface, based on the intensity-dependent three-dimensional image data, and
acquires the projection image data, based on values of the non-intensity-dependent three-dimensional image data corresponding to the voxel coordinates.

According to the present invention, whether it is a region where a measurement target is present or a region where it is not present, image data projected into a two-dimensional flat surface can be acquired by selecting a desired voxel from three-dimensional data for which roughly the same value is obtained.

Further features of the present invention will become apparent from the following description of exemplary embodiments with reference to the attached drawings.

DESCRIPTION OF THE EMBODIMENTS

The following provides an explanation of preferred embodiments of the present invention with reference to the drawings. However, the dimensions, materials and shapes of constituent parts described below, along with the relative arrangement thereof, may be suitably changed according to the configuration and various conditions of the apparatus to which the present invention is applied, and it is not intended to limit the scope of this invention to the following descriptions.

The present invention can be used when displaying three-dimensional data reflecting information on the properties within an object two-dimensionally. For example, the present invention can be used when acquiring information on the properties within an object by detecting acoustic waves propagating from the object. Accordingly, the present invention can be understood to be an object information acquiring apparatus or a method for the control thereof, or an object information acquisition method and signal processing method. In addition, the present invention can be understood to be a program that enables an information processing apparatus provided with a hardware resource such as a CPU to execute these methods, and a storage medium that stores that program.

The object information acquiring apparatus of the present invention includes an apparatus that uses photoacoustic tomography technology by which light (electromagnetic waves) is irradiated onto an object, and propagating acoustic waves generated within the object or on the surface of the object in accordance with photoacoustic effects are received (detected) at a plurality of measurement positions. Since information on the properties within an object is obtained in the form of image data and the like based on photoacoustic measurement, this type of object information acquiring apparatus is referred to as a photoacoustic imaging apparatus or photoacoustic image-forming apparatus. This type of object information acquiring apparatus may also be referred to as a photoacoustic tomography apparatus.

Property information in a photoacoustic device refers to the distribution of generation sources of acoustic waves generated as a result of radiation of light, the distribution of initial acoustic pressure in an object, the distribution of light energy absorption density or distribution of absorption coefficients derived from the initial acoustic pressure distribution, or the distribution of the concentrations of substances that composes a tissue. Specific examples thereof include the distribution of the concentrations of oxidized and reduced hemoglobin, distribution of blood components such as the distribution of oxygen saturation determined therefrom, and the distributions of fat, collagen or water. In addition, property information may be determined not as numerical data, but rather distribution data at each position within an object. Namely, distribution information such as absorption coefficient distribution or oxygen saturation distribution may be used as object information.

Acoustic waves as referred to in the present invention are typically ultrasonic waves, and include elastic waves referred to as sound waves or acoustic waves. Acoustic waves generated by photoacoustic effects are referred to as photoacoustic waves or photoultrasonic waves. Electrical signals converted from acoustic waves with a probe are also referred to as acoustic signals.

In photoacoustic imaging, intensity-dependent image data refers to a distribution that enables extraction of the structure of an absorbing body such as initial acoustic pressure distribution or absorption coefficient distribution. In addition, in photoacoustic imaging, non-intensity-dependent image data refers to a distribution of presence ratios in an object obtained based on signals corresponding to a plurality of wavelengths (for example, oxygen saturation distribution).

Here, an explanation is provided of a method for acquiring presence ratio distribution. In the case N types of substances are present, the absorption coefficient distribution $\mu_a(\lambda,X)$ of a coordinate $X=(x,y,z)$ obtained with pulsed light of a wavelength $\lambda$ is expressed in the manner of Equation (1).

$$\mu_a(\lambda,X)=\epsilon_1(\lambda)\cdot C_1(X)+\epsilon_2(\lambda)*C_2(X)+\ldots+\epsilon_N(\lambda)\cdot C_N(X) \quad (1)$$

Here, $\epsilon_n(\lambda)$ represents the absorption coefficient of substance n at wavelength $\lambda$, and $C_n(X)$ represents the amount of substance n present at coordinate X. Since $\epsilon_n(\lambda)$ is a definitive property, it can be acquired in advance. $\mu_a(\lambda,X)$ is obtained by an absorption coefficient distribution acquisition unit 6 to be subsequently described, and $C_n(X)$ is an unknown amount. Equation (1) is obtained for N types by obtaining each absorption coefficient distribution using pulsed light having N types of wavelengths, and since there are also N types of unknown amounts, N types of $C_n(X)$ can be acquired by solving simultaneous equations, and this becomes the concentration distribution of each substance.

Since concentration distribution is acquired according to the above-mentioned principle, it is acquired at not only coordinates where substances are present, but also at coordinates where substances are not present. The presence ratio of a substance k for n types of substances is expressed in the manner indicated below.

$$C_k \Big/ \sum_{n=1}^{N} C_n \quad \text{[Math. 1]}$$

The presence ratio of this substance k is such that, in principle, the value of a coordinate where substance k is not present and the value of a coordinate where substance k is present yield the same value even if S/N ratio is sufficiently high. Consequently, it is difficult to distinguish between coordinates where a substance is present and coordinates where it is not present based only on presence ratio.

For example, in the case of photoacoustic tomography, the ratio of the concentration of oxyhemoglobin to total hemoglobin concentration in the form of oxygen saturation distribution can be acquired as non-intensity-dependent three-dimensional image data.

In addition to property information obtained by photoacoustic effects, the present invention is effective during two-dimensional display of non-intensity-dependent three-dimensional image data for which a measurement target and noise have the same values in principle and it is difficult to distinguish between the two on the basis of voxel values (brightness) even if the S/N ratio is adequate for measurement. In ultrasound imaging, intensity-dependent data refers to image data that enables extraction of the structure of a measurement target, such as B mode images or echographic images, obtained by converting differences in acoustic impedance to images. In addition, in ultrasound imaging, non-intensity-dependent image data refers to, for example, color Doppler images representing blood flow. In addition, as is described in Embodiment 4, the distribution of vascular architecture information such as the angles or thicknesses of blood vessels obtained in vascular structure analyses using three-dimensional Hessian matrix also constitutes non-intensity-dependent image data.

Embodiment 1

Basic Embodiment

The following provides an explanation of a basic embodiment of the present invention. A description of constituent elements is first provided followed by a description of a method used to carry out the present embodiment and finally a description of the effects thereof.

<Apparatus Configuration>

Figure 1:
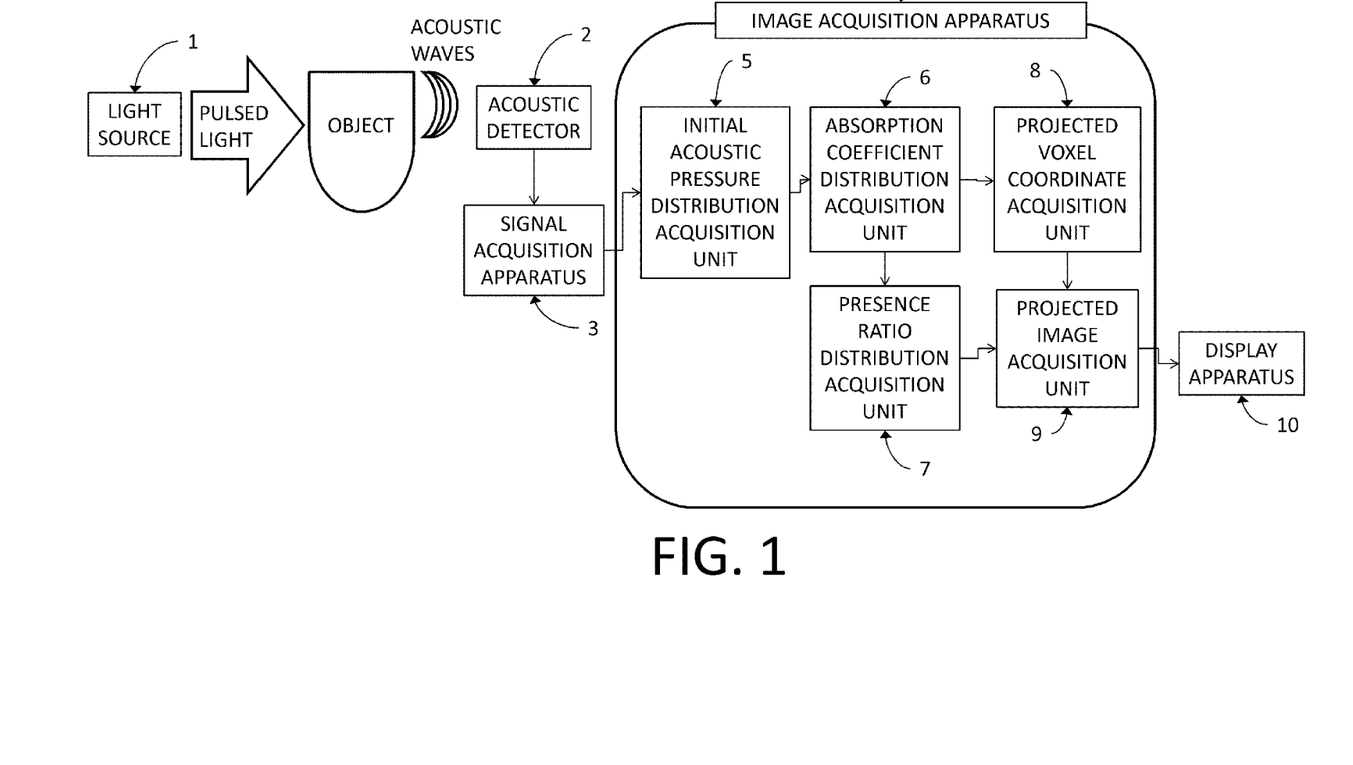
FIG. 1 is a schematic diagram showing the configuration of an apparatus according to Embodiment 1.

Constituent elements of the present invention are explained using FIG. 1. Constituent elements of the apparatus of the present invention are a light source 1, an acoustic detector 2, a signal acquisition apparatus 3, an image acquisition apparatus 4 and a display apparatus 10. The image acquisition apparatus 4 includes an initial acoustic pressure distribution acquisition unit 5, an absorption coefficient distribution acquisition unit 6, a presence ratio distribution acquisition unit 7, a projected voxel coordinate acquisition unit 8 and a projected image acquisition unit 9.

(Light Source)

The light source 1 is an apparatus that generates pulsed light. Although a laser is preferable for the light source in order to obtain a large output, a light-emitting diode and the like may also be used. Light must be irradiated for a sufficiently short period of time corresponding to the thermal properties of the object in order to efficiently generate photoacoustic waves. In the case the object is from the body, the pulse width of pulsed light generated from the light source is preferably several tens of nanoseconds or less. In addition, the wavelength of the pulsed light is within the near infrared region, which is referred to as the window to the body, and is preferably about 700 nm to 1200 nm. Since light of this region is able to reach comparatively deep parts of the body, information on deep parts of the body can be acquired. The wavelength of the pulsed light preferably has a high absorption coefficient with respect to the observation target. In addition, in the case of acquiring oxygen saturation, it is necessary to radiate pulsed light of a plurality of different wavelengths at different times. When pulsed light is irradiated onto an object, acoustic waves are generated from an absorbing body in the object such as blood due to photoacoustic effects.

(Acoustic Detector)

The acoustic detector 2 includes an acoustic detection element that converts acoustic waves that have been generated in and propagated through an object into electrical signals. In photoacoustic tomography, since three-dimensional imaging is carried out by receiving photoacoustic waves from a plurality of locations, either an object is scanned with a single acoustic detection element and moved to a plurality of measurement positions, or a plurality of acoustic detection elements are installed at separate locations and acoustic waves are received at a plurality of measurement positions. The acoustic detector 2 preferably has high sensitivity and a wide frequency range. More specifically, examples of acoustic detectors include PZT detectors, PVDF detectors, cMUT detectors and those using a Fabry-Perot interferometer. However, the acoustic detector is not limited to those listed here provided it satisfies the function of detecting propagated acoustic waves. The acoustic detector is equivalent to a receiver of the present invention.

(Signal Acquisition Apparatus)

The signal acquisition apparatus 3 converts electrical signals obtained with the acoustic detector 2 into amplitude and digital signals. More specifically, the signal acquisition apparatus 3 includes an amplifier, analog-digital converter (ADC) and the like formed of electrical circuits. In order to acquire data efficiently, the number of amplifiers and ADC is preferably equal to the number of receiving elements of the acoustic detector 2. However, individually provided amplifiers and ADC may also be used by reconnecting in order.

(Image Acquisition Apparatus)

The image acquisition apparatus 4 acquires images obtained by projecting data indicating object internal property information onto a two-dimensional flat surface from digital signals obtained with the signal acquisition apparatus 3. Here, three-dimensional oxygen saturation data is used for the data. More specifically, the image acquisition apparatus 4 is formed of a digital signal processing apparatus such as a computer or FPGA, and a computational circuit or CPU carries out information processing by operating in accordance with a program. The image acquisition apparatus 4 is formed of the initial acoustic pressure distribution acquisition unit 5, the absorption coefficient distribution acquisition unit 6, the presence ratio distribution acquisition unit 7, the projected voxel coordinate acquisition unit 8 and the projected image acquisition unit 9. The image acquisition apparatus is equivalent to a processor of the present invention.

(Initial Acoustic Pressure Distribution Acquisition Unit)

The initial acoustic pressure distribution acquisition unit 5 acquires the distribution of initial acoustic pressure in the form of a three-dimensional image indicating the initial acoustic pressure at the sound source by reconfiguring digitized signals. A single initial acoustic pressure distribution is acquired for each wavelength of the light source. Although the reconfiguration processing method is preferably universal back projection in which differentially processed signals are superimposed after back-propagating from the position where a signal was obtained, any method may be used provided it enables images to be reconfigured. Initial acoustic pressure distribution is intensity-dependent information since the values of the measurement target and noise component differ enabling both to be distinguished provided the S/N ratio is sufficiently high.

(Absorption Coefficient Distribution Acquisition Unit)

The absorption coefficient distribution acquisition unit 6 acquires the distribution of absorption coefficients within an object by calculating attenuation of light that has entered the object and dividing the initial acoustic pressure distribution by light distribution. Acoustic pressure p of a photoacoustic wave is dependent on light intensity $\phi$ as represented by the relationship of Equation (2).

$$p = \Gamma \cdot \phi \cdot \mu_a \quad (2)$$

Here, $\Gamma$ represents the Grueneisen constant and $\mu_a$ represents absorption coefficient.

When light enters an object, the light is scattered by the base material of the object and absorbed, and light intensity decreases exponentially corresponding to the propagation distance. The distribution of light intensity within an object is obtained from the intensity distribution of light irradiated onto the object and the shape of the object. Since light intensity distribution within an object differs according to the wavelength of the light, it is required to be calculated for each light source. In addition, the Grueneisen constant can be considered to be constant in the case of the human body. Thus, absorption coefficient distribution is obtained by dividing initial acoustic pressure distribution by light intensity distribution and the Grueneisen constant $\Gamma$. Absorption coefficient distribution is obtained without having to divide by the Grueneisen constant if only using relative values. Absorption coefficient distribution is intensity-dependent information since the values of the measurement target and noise component differ enabling both to be distinguished provided the S/N ratio is sufficiently high.

(Presence Ratio Distribution Acquisition Unit)

The presence ratio distribution acquisition unit 7 acquires the distribution of the presence ratios of substances by comparative processing of a plurality of absorption coefficient distributions obtained at a plurality of wavelengths. In the case of determining oxygen saturation, it is necessary to carry out arithmetic processing after the plurality of absorption coefficient distributions are all present. Therefore, once the absorption coefficient distribution has been acquired by measurement according to a first wavelength, that data is preferably stored within the apparatus or in external memory. Arithmetic processing is then carried out together with the absorption coefficient distribution obtained by measurement according to a second wavelength.

In addition, although coordinate systems such as the scale, offset and orientation of the absorption coefficient distribution and presence ratio distribution are aligned in order to acquire those distributions, in general, the coordinate systems of intensity-dependent information and non-intensity-dependent information do not necessarily align. In the case the scales and coordinates thereof differ, it is necessary to align the coordinate systems by carrying out image processing on either the intensity-dependent information or non-intensity-dependent information. Images for which coordinate systems have been aligned are used in the projected voxel coordinate acquisition unit 8 and the projected image acquisition unit 9. As a result, the intensity-dependent information or non-intensity-dependent information is correctly reflected in projection image data.

(Projected Voxel Coordinate Acquisition Unit)

The projected voxel coordinate acquisition unit 8 acquires the coordinates of contributing voxels when projecting a three-dimensional image of absorption coefficient distribution on a two-dimensional flat surface. Since an absorption coefficient distribution for pulsed light of each wavelength is obtained with the absorption coefficient distribution acquisition unit 6, while there is only one absorption coefficient distribution used in the projected voxel coordinate acquisition unit 8, it is necessary to determine one absorption coefficient distribution to be used here among the resulting absorption coefficient distributions. Since coefficient absorption distributions obtained regardless of the presence ratio of each absorbing body are the same in the case the absorption coefficients of each absorbing body are the same, a wavelength is selected such that the absorption coefficient of each absorbing body is as close as possible, and the absorption coefficient distribution for that wavelength is used preferably. In addition, in consideration of the wavelength dependency of the absorption coefficients of each absorbing body, a wavelength desired to be projected may be selected and the absorption coefficient distribution for that wavelength may be used.

The above-mentioned selection may be made manually by a user or may be determined automatically in accordance with conditions. In addition, in order to facilitate acquisition of voxel coordinates contributing to projection, image processing such as noise reduction or enhancement processing may be carried out on absorption coefficient distributions, and this may be used to determine voxel coordinates contributing to projection.

Figure 2A:
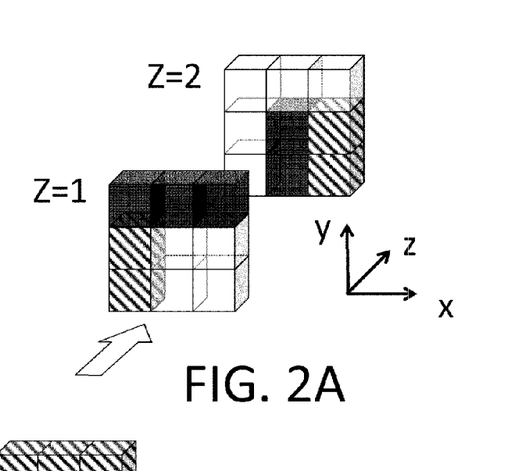
FIGS. 2A to 2E are schematic diagrams for explaining an image acquisition method of Embodiment 1.
Figure 2B:
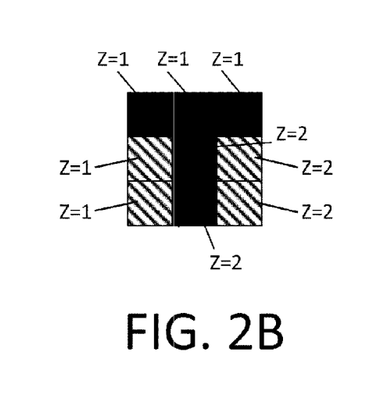

FIGS. 2(a) and 2(b) are drawings representing a method for acquiring projection image data by MIP. In the drawings, a total of 18 voxels are indicated including 3×3 voxels in the X and Y directions and 2 voxels in the Z direction. The color of each voxel is such that a darker color indicates a higher value. The projecting direction is the Z direction. Namely, a single pixel value of a two-dimensional image is determined based on each voxel value superimposed in the Z direction.

In the case of using MIP for the projection method in FIG. 2(a), the voxel having the maximum absorption coefficient among the plurality of voxels in the projecting direction of the Z direction is projected. Thus, when MIP is used, a projected image is obtained in the manner of FIG. 2(b). The color in FIG. 2(b) indicates the color of the projected image, and the numbers shown within each voxel indicate the coordinates of the contributing voxels. The projected voxel coordinate acquisition unit 8 acquires the coordinates of voxels contributing to the acquisition of projection image data.

Although MIP is acquired here for the sake of explanation, it is not necessarily required to acquire MIP since it is only necessary to obtain those coordinates contributing to projection. In addition, the projection is not limited to MIP that projects maximum values, but rather a method may be used that projects the minimum value, median value or mode and the like of a plurality of voxels in the projecting direction. The projected voxel coordinate acquisition unit 8 acquires the coordinates of contributing voxels even in the case of using these values instead of MIP.

In addition, in the case there is a plurality of voxels having a maximum value and the like among voxels in the projecting direction, it is necessary to decide on one of those voxels. In this case, since the absorbing body is continuously present spatially, the selected voxel is preferably spatially continuous. Therefore, if the projecting direction is assumed to be the Z direction, voxels in proximity to each candidate voxel in the X-Y plane are confirmed, and a voxel is preferably selected for which a voxel contributing to projection that is present in the vicinity thereof. In addition, a voxel may also be selected for which a voxel of about the same value is present in the vicinity of that voxel. In addition, a voxel may also be determined according to the location at which it appears, such as the voxel that appears first or the voxel that appears last among a plurality of voxels having a maximum value and the like.

(Projected Image Acquisition Unit)

Figure 2C:
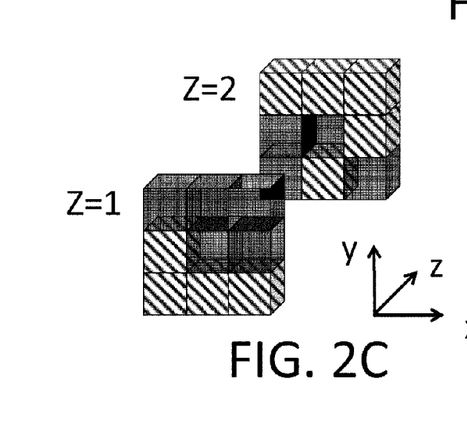
Figure 2D:
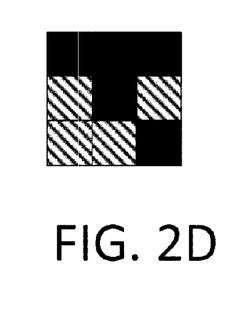

The projected image acquisition unit 9 acquires the values of voxels corresponding to the coordinates obtained with the projected voxel coordinate acquisition unit 8 among the presence ratio distributions obtained with the presence ratio distribution acquisition unit 7. In the case of having obtained presence ratio distributions as shown in FIG. 2(c), values obtained by referencing each coordinate in the X-Y plane that is perpendicular to the projecting direction are assigned by referring to the values of the presence ratio distributions corresponding to the coordinates of the voxels shown in FIG. 2(b). FIG. 2(d) shows the projected image obtained as a result thereof. According to this technique, an image is obtained that reflects the presence ratio of an observation target image, thereby facilitating ascertainment of the three-dimensional presence ratio distribution of a measurement target image on a two-dimensional flat surface.

Figure 2E:
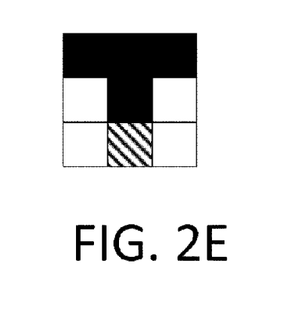

Moreover, a projected image of presence ratio distribution is preferably acquired using only the voxels of an observation target image by establishing a threshold value that enables separation of the observation target image and noise component in an absorption coefficient distribution, and then labeling the voxels of the observation target image and noise component. For example, in FIG. 2(e), the voxel value (absorption coefficient value) corresponding to the darkest color in FIG. 2(a) is used as a prescribed threshold value. The result is a two-dimensional image in the case of using voxels having a value larger than this prescribed threshold value for a projected image, and not using the presence ratio values of voxels having a value lower than this threshold value. At this time, images are acquired by representing values of presence ratios with a certain color distribution, and assigning voxels that are not observation target images to colors not used in presence ratios. As a result, values of presence ratio distribution can be reflected in the structure of absorption coefficient distribution, and three-dimensional structure and properties can be ascertained two-dimensionally. In addition, absorption coefficient distributions that have been subjected to image processing may be used in labeling to facilitate separation of the observation target image and noise component. In addition, labeling is not required to use a method using a threshold value, but rather any method may be used provided it enables division of regions.

(Display Apparatus)

The display apparatus 10 is an apparatus that displays projected images obtained by the projected image acquisition unit 9. More specifically, the display apparatus 10 is a display and the like. Although images are preferably displayed in color, they may also be displayed in black and white. The display apparatus is able to express intensity of information distribution as a degree of brightness.

<Processing Flow>

Figure 3:
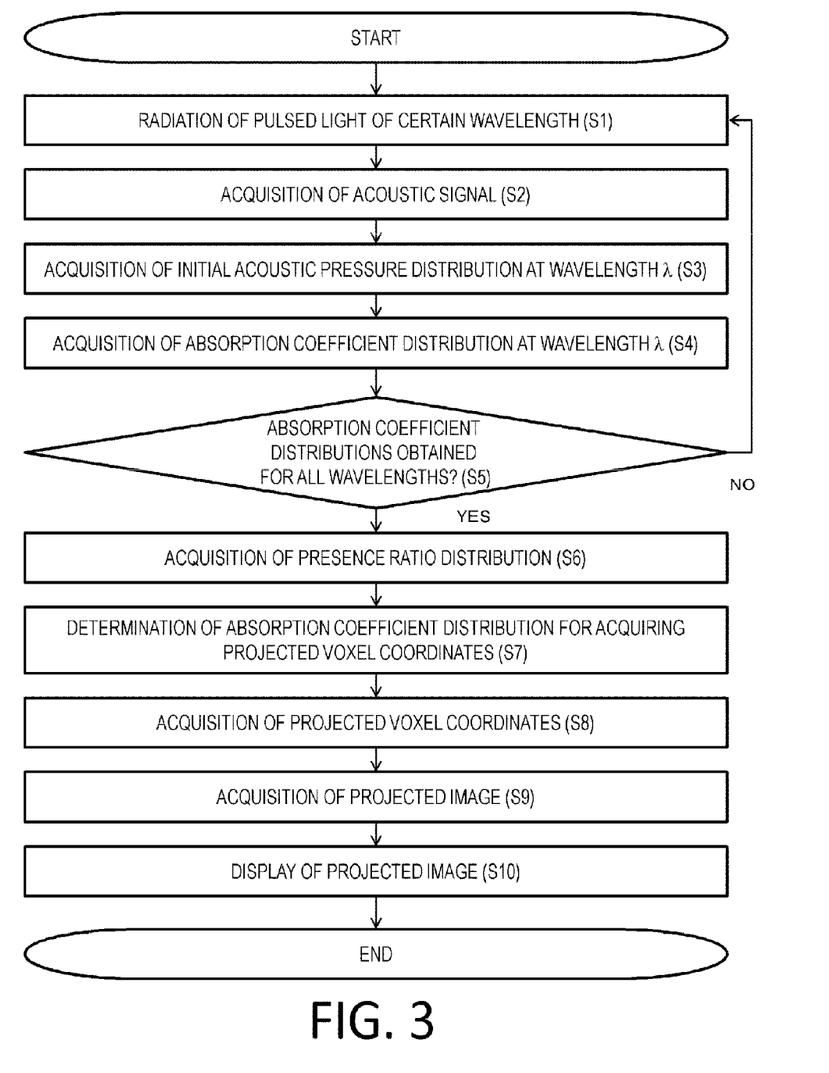
FIG. 3 is a flow chart showing a method for carrying out Embodiment 1.

An explanation of a method for carrying out the present invention is provided in line with each of the steps of the flow chart shown in FIG. 3.

First, the light source radiates pulsed light of a certain wavelength (S1). The wavelength $\lambda$ at this time is equal to $\lambda_1$. At this time, acoustic waves generated from an object are received by the acoustic detector and converted to acoustic signals (electrical signals) (S2). Next, the initial acoustic pressure distribution acquisition unit carries out reconfiguration and acquires the initial acoustic pressure distribution at wavelength $\lambda = \lambda_1$ (S3). Light distribution is corrected in the absorption coefficient distribution acquisition unit to acquire the absorption coefficient distribution for wavelength $\lambda$ (S4).

A determination is then made as to whether or not absorption coefficient distributions have been obtained for all predetermined wavelengths (S5). If all absorption coefficient distributions have not been obtained, the wavelength of the pulsed light is changed (such as by changing wavelength $\lambda$ from $\lambda_1$ to $\lambda_2$) and steps S1 to S4 are carried out again. In the case absorption coefficient distributions have been obtained for all wavelengths, the presence ratio distribution acquisition unit acquires presence ratio distributions using the resulting absorption coefficient distributions (S6). Next, the projected voxel coordination acquisition unit determines the absorption coefficient distribution used when determining voxel coordinates that contribute to a projected image (S7), and acquires the coordinates of voxels that contribute when projected for the determined coefficient absorption distribution (S8). The projected image acquisition unit then acquires a projected image using presence ratio distribution values (S9). The display apparatus then displays the projected image (S10).

According to the apparatus of the present embodiment, even in the case of non-brightness-dependent information that does not reflect structural information, a projected image can be acquired in consideration of the structure of a measurement target image, thereby enabling three-dimensional information to be ascertained on a two-dimensional image. In addition, since the values of non-intensity-dependent information are projected as is, non-brightness-dependent information can be accurately determined. Thus, in the case a blood vessel is the measurement target, a presence ratio indicating the properties of the blood vessel can be reflected in a projected image obtained by projecting the three-dimensional structure two-dimensionally, thereby making it possible to simultaneously determine three-dimensional vascular structure and vascular properties.

Embodiment 2

Acquisition of Slab MIP

In the present invention, a description is provided of a method for acquiring a plurality of projected images projecting a portion of a three-dimensional image by changing the projection range in order to facilitate a detailed understanding of three-dimensional structure.

Figure 4:
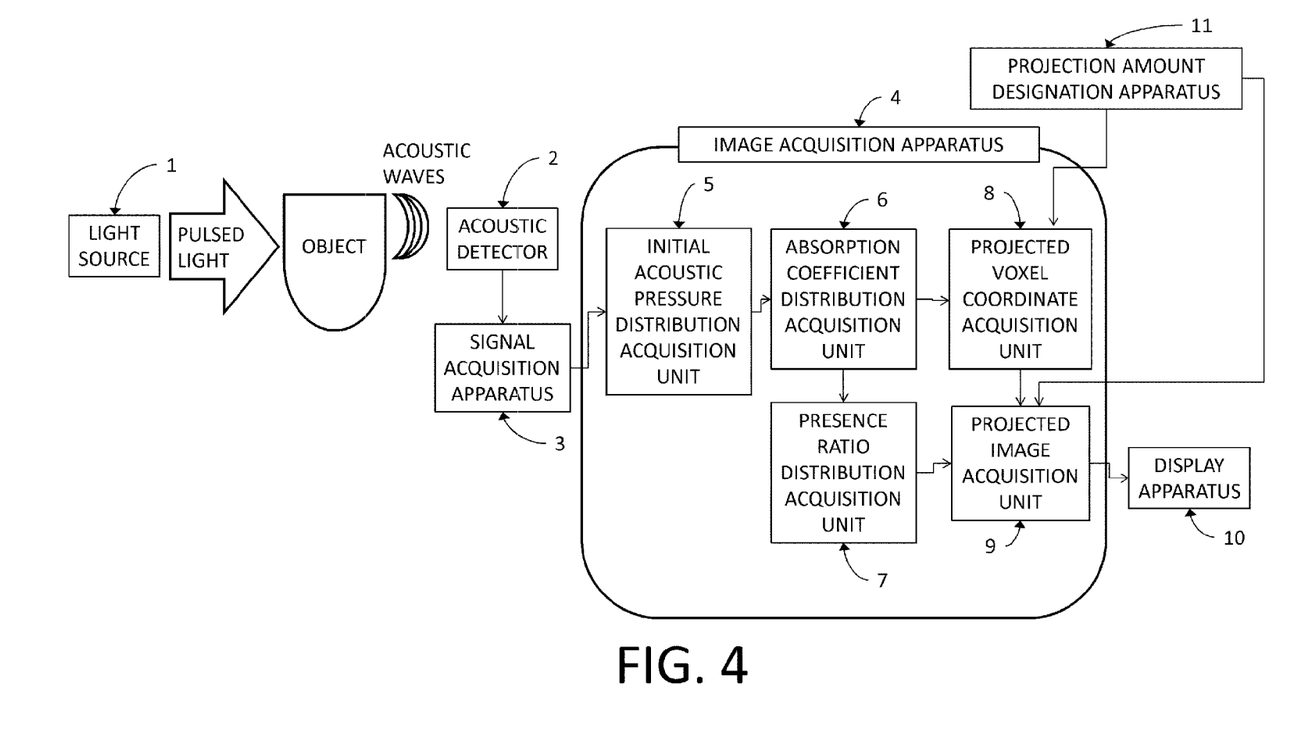
FIG. 4 is a schematic diagram showing the configuration of an apparatus according to Embodiment 2.

The apparatus of the present invention has a projection amount designation apparatus 11 in addition to the constituent elements of Embodiment 1 as shown in FIG. 4. The projection amount designation apparatus designates thickness in the projecting direction (projected amount) when projecting three-dimensional images. More specifically, in the case a user inputs a projected amount manually, this apparatus is an input apparatus such as a keyboard, mouse or dial. In addition, although the method described here includes designating the projected amount manually, the projected amount may also be determined in advance or may be determined automatically together with the size of three-dimensional data.

The projected voxel coordinate acquisition unit 8 and the projected image acquisition unit 9 of the present embodiment carry out processing based on a projected amount t designated by the projection amount designation apparatus 11. Furthermore, the projecting direction here is the Z direction. The projected voxel coordinate acquisition unit 8 first acquires coordinates of contributing voxels when projecting over a range of Z=1 to t−1 from a three-dimensional image in the form of an absorption coefficient distribution. The projected voxel coordinate acquisition unit next acquires the coordinates of contributing voxels when projecting over a range of Z=2 to t. Moreover, the coordinates of contributing voxels are then acquired over the range of Z=3 to t+1. In this manner, the coordinates of contributing voxels are acquired when projecting a three-dimensional image on a two-dimensional flat surface over each range while shifting the range one voxel at a time. The above procedure is repeated until the terminal coordinates in the Z direction are included in the range.

Similarly, the projected image acquisition unit 9 projects images by acquiring the values of voxel coordinates obtained with the projected voxel coordinate acquisition unit 8 from among presence ratio distributions in each range, and acquires a single projected image for each range. As a result, a number of projected images are acquired that is one voxel less than the number of voxels in the projecting direction of the absorption coefficient distributions and presence ratio distributions. A three-dimensional image is formed if these projected images are arranged in a row in the projecting direction. Since the display apparatus 10 is a two-dimensional flat surface, a single arbitrary projected image is selected from among the three-dimensional images and displayed. The projected image is preferably able to be selected by a user.

The flow of the present embodiment has an additional step for designating the projected amount in comparison with Embodiment 1. This step may be carried out at any point prior to S8 of FIG. 3.

According to the apparatus of the present embodiment, since the number of superimposed structures can be reduced by projecting over a partial range, details of the three-dimensional structure of non-intensity-dependent information can be easily ascertained.

Furthermore, the projected voxel coordinate acquisition unit 8 may also acquire coordinates of contributing voxels when a three-dimensional image has been projected on a two-dimensional flat surface on the basis of a single projected image based on the projection amount designated by the projection amount designation apparatus 11. In addition, the projection amount designation apparatus 11 may designate the projected amount for three-dimensional image data in which non-intensity-dependent three-dimensional image data is represented using lightness for the values of intensity-dependent three-dimensional image data.

Embodiment 3

Gradation Display

In the present embodiment, a description is provided of a method for displaying three-dimensional structures of non-intensity-dependent information, in addition to a display method that facilitates acknowledging the reliability thereof.

Figure 5:
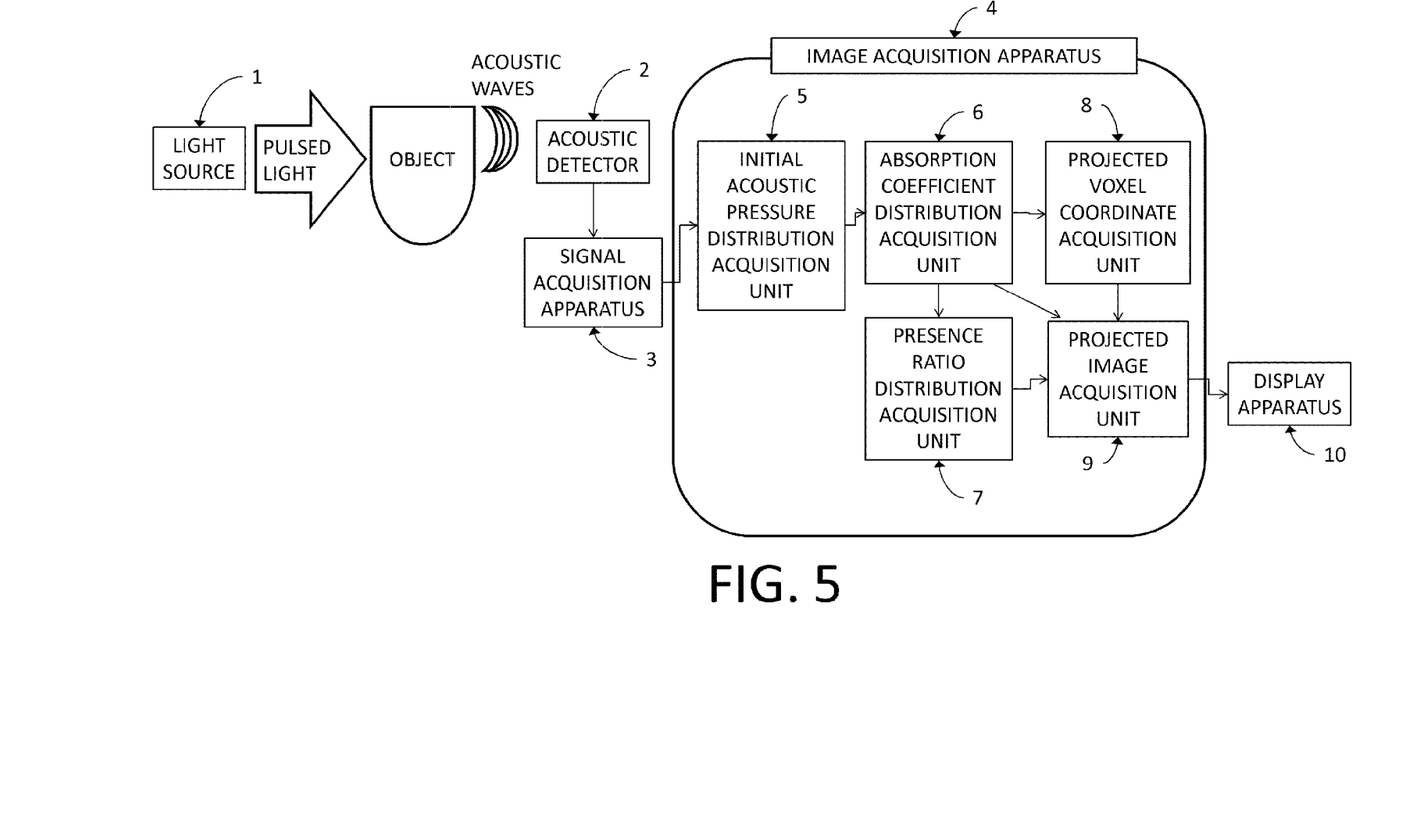
FIG. 5 is a schematic diagram showing the configuration of an apparatus according to Embodiment 3.

The constituent elements per se of the apparatus of the present embodiment are the same as those of Embodiment 1. However, as shown in FIG. 5, an arrow is added from the absorption coefficient distribution acquisition unit 6 to the projected image acquisition unit 9, and the processing content is different in the projected image acquisition unit 9.

Although the projected image acquisition unit 9 of the present embodiment acquires projected images by projecting values of presence ratio distributions in coordinates obtained with the projected voxel coordinate acquisition unit 8 in the same manner as Embodiment 1, image acquisition is carried out by also referencing the values of absorption coefficient distributions at the same coordinates at that time. Since absorption coefficient distributions are intensity-dependent information, the possibility of being a measurement target image increases as values become larger. In addition, since absorption coefficient distributions constitute data that serves as the basis of presence ratio distributions, the reliability of a presence ratio distribution can be said to be high if the value thereof is high. Thus, the reliability of a presence ratio distribution, or in other words non-intensity-dependent information, can be indicated by considering absorption coefficient distribution, or in other words, intensity-dependent information serving as the basis of non-intensity-dependent information.

The method used to acquire a projected image includes assigning a presence ratio and absorption coefficient corresponding to the projected coordinates to any two of color hue, lightness and chroma and acquiring an image based on the colors of those coordinates. Colors are preferably acquired by assigning presence ratio values to hue and assigning absorption coefficients to lightness, and two sets of information can be easily perceived and expressed with a single color.

According to the apparatus of the present embodiment, projected images can be acquired in which a presence ratio and absorption coefficient, which indicates the reliability of the presence ratio, can be determined at a glance, thereby facilitating understanding of presence ratio.

Embodiment 4

Vascular Architecture, Angle and Thickness

In the present embodiment, a description is provided of the case of handling non-intensity-dependent information other than presence ratio in a photoacoustic device.

In the case of using pulsed light of the near infrared range, for which blood accounts for the primary absorption thereof, in a photoacoustic apparatus, the resulting absorption coefficient distribution indicates vascular structure. Angle, thickness and other blood vessel parameters of vascular architecture information can be extracted by carrying out processing, in which vascular structure is analyzed using a three-dimensional Hessian matrix, on this absorption coefficient distribution. Processing for analyzing vascular structure using a three-dimensional Hessian matrix is carried out regardless of whether the processing target is a vascular component or noise component, and blood vessel angle, thickness and other vascular architecture information has the same values as vascular and noise components even if the S/N ratio is adequate. Thus, vascular architecture information constitutes non-intensity-dependent information.

The constituent elements of the present embodiment are the same as those of Embodiments 1 to 3 with the exception of using a vascular architecture information acquisition unit instead of the presence ratio distribution acquisition unit 7. The vascular architecture information acquisition unit acquires a Hessian matrix from the intensity gradient of a voxel of interest and surrounding voxels, and analyzes the type of structure formed by the voxel of interest from their intrinsic values and intrinsic vectors. As a result of carrying out this analysis on all voxels, the distributions of line angles, line thicknesses and the like are obtained. Line angles and line thicknesses constitute non-intensity-dependent information. A projected image can then be acquired for three-dimensional vascular architecture by using this non-intensity-dependent information instead of the presence ratio distribution of Embodiments 1 to 3.

Moreover, line likeness indicating the possibility of the voxel of interest being a portion of a linear structure can be acquired by carrying out arithmetic processing using intrinsic values of the Hessian matrix of the voxel of interest during the course of obtaining vascular architecture information. Line likeness constitutes intensity-dependent information in which the values of the measurement target image and noise component differ in the case of an adequate S/N ratio. Thus, the projected voxel coordinate acquisition unit 8 may use the distribution of line likeness obtained as a result of having analyzed a vascular structure instead of using absorption coefficient distribution. As a result, since voxels that do not form linear structures have small values, a projected image of non-intensity-dependent information can be acquired based on intensity-dependent information having a high S/N ratio for which linear structure has been enhanced.

Figure 6:
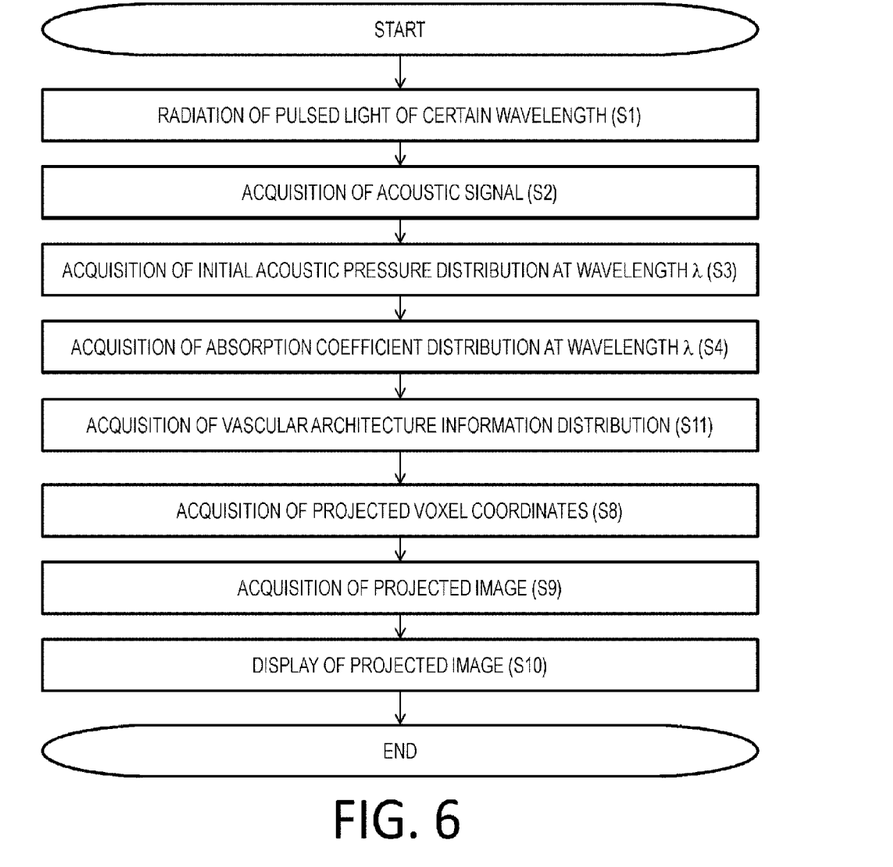
FIG. 6 is a flow chart showing a method for carrying out Embodiment 4.

In the present embodiment, since one type of pulsed light is sufficient, the method for carrying out the present embodiment is as shown in the flow chart of FIG. 6. An explanation thereof is provided while focusing on differences with FIG. 3. The absorption coefficient distribution acquisition unit acquires an absorption coefficient distribution using pulsed light of a certain prescribed wavelength (S4). The above-mentioned vascular architecture information acquisition unit acquires a vascular architecture information distribution from the absorption coefficient distribution thereof (S11). The projected voxel coordinate acquisition unit acquires projected voxel coordinates from the absorption coefficient distribution (S8). The projected image acquisition unit acquires a projected image using the vascular architecture information distribution (S9). Line likeness distribution obtained simultaneous to acquisition of vascular architecture information distribution may also be used in the acquisition of projected voxel coordinates (S8).

According to the apparatus of the present embodiment, projected images can be acquired that are obtained by two-dimensionally projecting three-dimensional vascular architecture information, thereby facilitating understanding of quantitative vascular architecture information.

Embodiment 5

Color Doppler

A description is provided of the case of using color Doppler images indicating non-intensity-dependent information in the form of blood flow by using three-dimensional B-mode images indicating intensity-dependent information in the form of acoustic impedance distribution in an ultrasound diagnostic apparatus.

Figure 7:
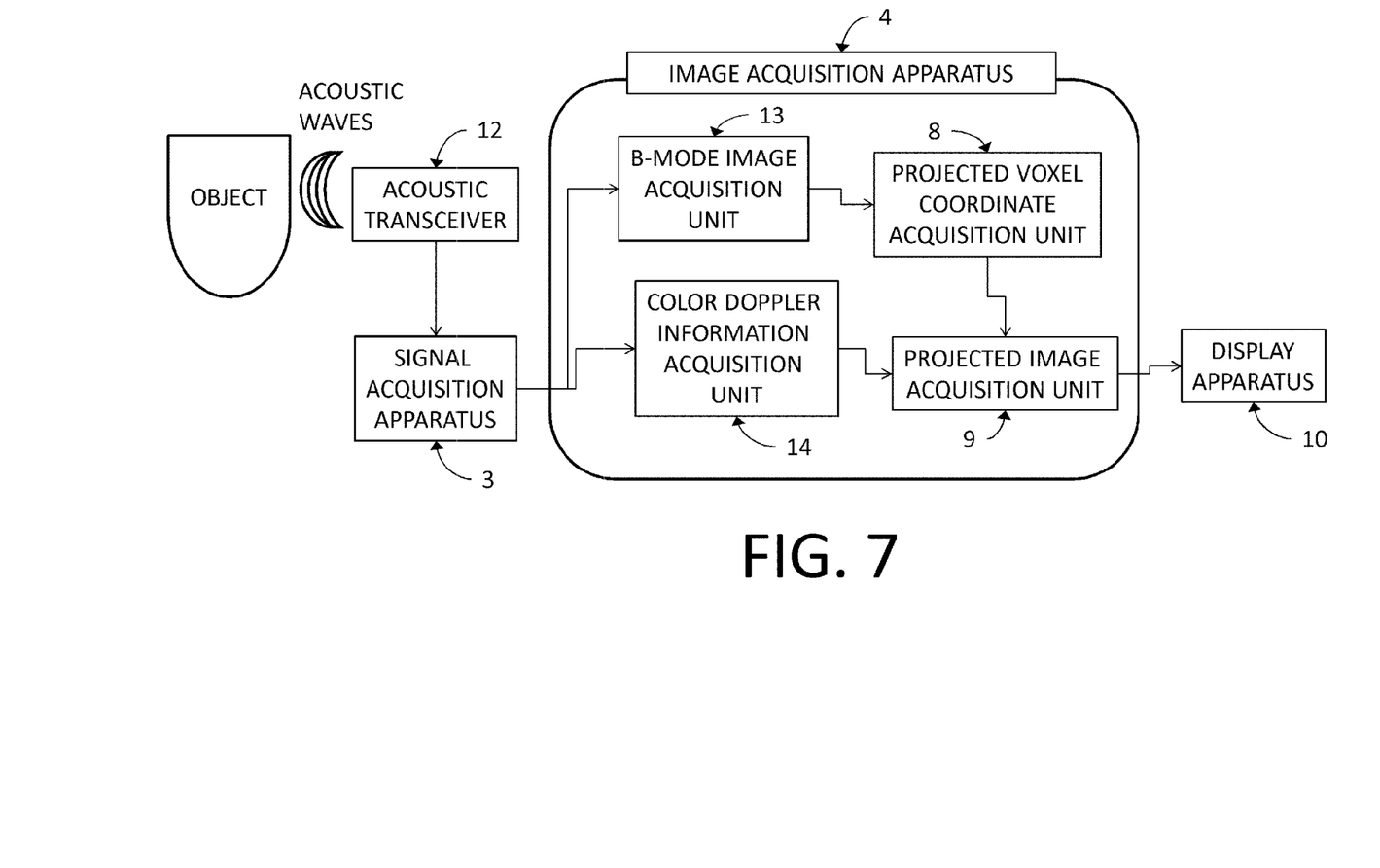
FIG. 7 is a schematic diagram showing the configuration of an apparatus according to Embodiment 5.

Constituent elements of the present embodiment are shown in FIG. 7. An acoustic transceiver 11 transmits and receives acoustic waves. The acoustic transceiver transmits ultrasonic waves towards an object, receives ultrasonic waves that have been reflected from within the object, and converts the ultrasonic waves to electrical signals. Similar to photoacoustic tomography, three-dimensional imaging is carried out in the present embodiment by receiving acoustic waves from a plurality of locations. Consequently, acoustic waves are received at a plurality of locations by scanning the object with a single acoustic transceiver element and moving it to multiple locations or installing a plurality of acoustic transceiver elements at separate locations.

The acoustic transceiver 11 preferably has high sensitivity and a high wide frequency range, and more specifically, examples of acoustic transceivers include PZT transceivers, PVDF transceivers, cMUT transceivers and those using a Fabry-Perot interferometer. However, the acoustic transceiver is not limited to those listed here, and may be any acoustic transceiver provided it satisfies the function of transmitting and receiving acoustic waves. The signal acquisition apparatus 3 amplifies received electrical signals and converts them to digital signals in the same manner as Embodiment 1.

The image acquisition apparatus 4 of the present embodiment includes as characteristic constituent elements thereof a B-mode image acquisition unit 13 and a color Doppler information acquisition unit 14. In the B-mode image acquisition unit 12, three-dimensional B-mode images are acquired using digital signals obtained with the signal acquisition apparatus 3. The delay and sum method, by which images are acquired using delay and overlapping processing using signals obtained at a plurality of positions, is preferably used for the method of acquiring three-dimensional B-mode images. However, the method is not limited thereto, and any method may be used provided it allows the acquisition of three-dimensional B-mode images. Although values are obtained for all voxels, since the noise component and measurement target image have different values provided the S/N ratio is adequate, B-mode images constitute intensity-dependent information.

The color Doppler information acquisition unit 13 acquires three-dimensional color Doppler images using digital signals obtained with the signal acquisition apparatus 3. Color Doppler images are obtained by calculating differences in signal frequencies using an autocorrelation function and transmission/reception repeat time of each signal obtained by transmitting and receiving acoustic waves a plurality of times at a constant time interval. When acquiring color Doppler images, the relative phase difference of a plurality of signals is observed. Consequently, since the noise component and measurement target image have the same values even if adequate S/N ratios have been obtained in individual measurements, color Doppler images constitute non-intensity-dependent information. At this time, processing for aligning the scales and coordinates of B-mode images and color Doppler images is carried out in the case they differ.

The projected voxel coordinate acquisition unit 8, the projected image acquisition unit 9 and the display apparatus 10 are the same as in Embodiments 1 to 4. Namely, the projected voxel coordinate acquisition unit 8 acquires the coordinates of contributing voxels when projecting a three-dimensional B-mode image. The projected image acquisition unit 9 acquires a projected image using the value of the color Doppler image of the resulting coordinates. The acquired projected image is then displayed on the display apparatus 10.

Figure 8:
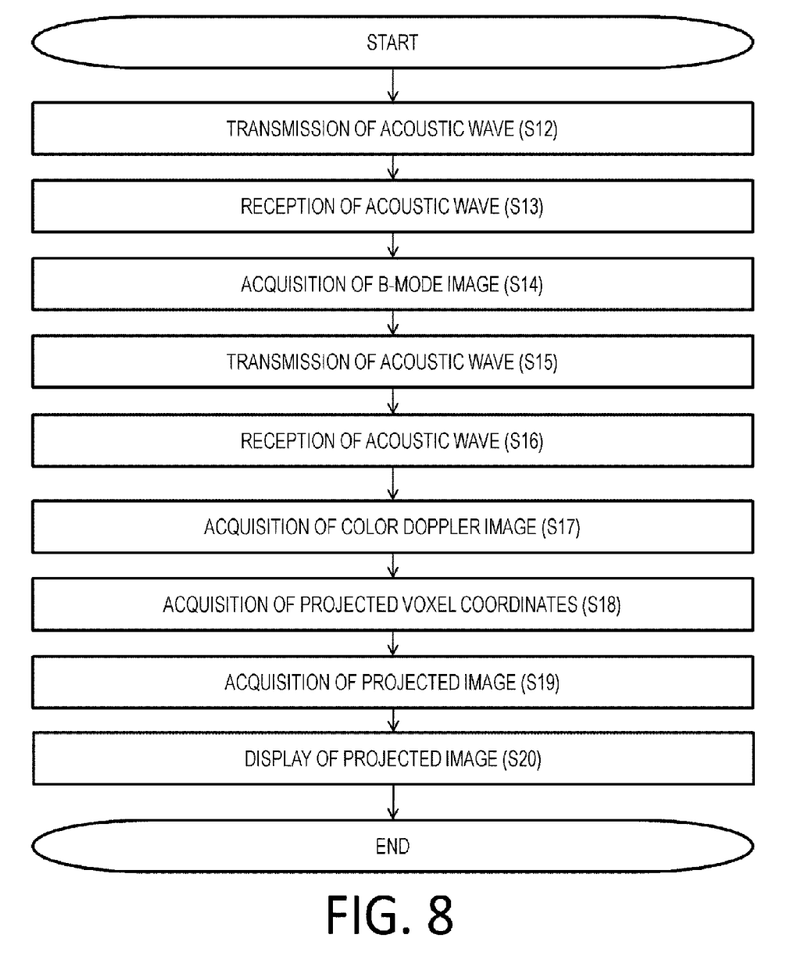
FIG. 8 is a flow chart showing a method for carrying out Embodiment 5.

An explanation of the method for carrying out the present embodiment is provided using the flow chart of FIG. 8.

First, the acoustic transceiver 11 transmits a first transmitted acoustic wave (S12) and receives a first reflected acoustic wave that has been reflected from an object (S13). The B-mode image acquisition unit then acquires a B-mode image using the first reflected acoustic wave (S14). Next, the acoustic transceiver 11 transmits a second transmitted acoustic wave (S15) after the elapse of a fixed amount of time since transmitting the first transmitted acoustic wave (S12), and receives a second reflected acoustic wave that has been reflected from the object (S16).

The color Doppler information acquisition unit acquires a color Doppler image using the first reflected acoustic wave, the second reflected acoustic wave and the time interval from S12 to S15 (S17). The projected voxel coordinate acquisition unit acquires projected voxel coordinates from the B-mode image (S18). The projected image acquisition unit acquires a projected image using the projected voxel coordinates and the color Doppler image (S19). The display apparatus then displays the projected image (S20).

According to the apparatus of the present embodiment, projected images can be acquired that are obtained by two-dimensionally projecting three-dimensional blood flow information, thereby facilitating understanding of vascular structure and blood flow information.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-108040, filed on May 26, 2014, which is hereby incorporated by reference wherein in its entirety.

What is claimed is:

1. An object information acquiring apparatus, comprising:
 a receiver that receives acoustic waves propagating through an object at a plurality of measurement positions; and
 a processor that acquires projection image data obtained by projecting on a two-dimensional flat surface a distribution of property information relating to a measurement target within the object, wherein
 the processor
  acquires intensity-dependent three-dimensional image data within the object and non-intensity-dependent three-dimensional image data within the object, based on the acoustic waves,
  determines voxel coordinates projected onto the two-dimensional flat surface, based on the intensity-dependent three-dimensional image data, and
  acquires the projection image data, based on values of the non-intensity-dependent three-dimensional image data corresponding to the voxel coordinates.

2. The object information acquiring apparatus according to claim 1, wherein the processor determines the voxel coordinates by selecting a voxel, for which the size of the value thereof reaches a maximum, from among voxels in a projecting direction when acquiring the projection image data.

3. The object information acquiring apparatus according to claim 2, wherein the processor projects the non-intensity-dependent three-dimensional image data for a voxel corresponding to an image of a measurement target within the object.

4. The object information acquiring apparatus according to claim 3, wherein the processor projects the non-intensity-dependent three-dimensional image data for a voxel for which the size of the value thereof in the intensity-dependent three-dimensional image data is greater than a prescribed threshold value.

5. The object information acquiring apparatus according to claim 1, wherein the processor acquires, for the determined voxel coordinates, the projection image data by assigning any of hue, lightness and chroma to the intensity-dependent three-dimensional image data, and assigning any of the hue, lightness and chroma not used for the intensity-dependent three-dimensional image data to the non-intensity-dependent three-dimensional data.

6. The object information acquiring apparatus according to claim 1, further comprising a projection amount designator that determines a range of voxels in the projecting direction when acquiring the projection image data.

7. The object information acquiring apparatus according to claim 6, wherein the processor acquires three-dimensional image data by acquiring a plurality of sets of projection image data while shifting the range of voxels determined by the projection amount designator by one voxel at a time.

8. The object information acquiring apparatus according to claim 1, wherein the processor aligns the intensity-dependent three-dimensional image data with a coordinate system of the non-intensity-dependent three-dimensional image data.

9. The object information acquiring apparatus according to claim 1, wherein the intensity-dependent three-dimensional image data is data that enables an image of a measurement target within an object to be distinguished from noise according to the size of a value, and the non-intensity-dependent three-dimensional image data is data for which it is difficult to distinguish between an image of the measurement target and noise according to the size of a value.

10. The object information acquiring apparatus according to claim 1, wherein the non-intensity-dependent three-dimensional image data is a distribution of presence ratios of substances that compose the object.

11. The object information acquiring apparatus according to claim 1, further comprising a display that displays the projection image data.

12. An object information acquiring apparatus, comprising:
a processor that
acquires intensity-dependent three-dimensional image data within an object, based on acoustic waves which are generated from the object,
acquires non-intensity-dependent three-dimensional image data within the object, based on the acoustic waves,
determines voxel coordinates projected onto a projection plane, based on the intensity-dependent three-dimensional image data, and
acquires projection image data by projecting, on the projection plane, the non-intensity-dependent three-dimensional image data corresponding to the voxel coordinates.

13. The object information acquiring apparatus according to claim 12, wherein the processor determines the voxel coordinates by selecting a voxel, for which a value of the intensity-dependent three-dimensional image data reaches a maximum, from among voxels in a projecting direction when acquiring the projection image data.

14. The object information acquiring apparatus according to claim 12, wherein the processor determines the voxel coordinates by selecting a voxel corresponding to an image of a measurement target within the object in the intensity-dependent three-dimensional image data.

15. The object information acquiring apparatus according to claim 12, wherein the processor determines the voxel coordinates by selecting a voxel for which a value of the intensity-dependent three-dimensional image data is greater than a prescribed threshold value.

16. The object information acquiring apparatus according to claim 12, wherein the processor acquires, for the determined voxel coordinates, the projection image data by assigning any of hue, lightness and chroma to the intensity-dependent three-dimensional image data, and assigning any of the hue, lightness and chroma not used for the intensity-dependent three-dimensional image data to the non-intensity-dependent three-dimensional data.

17. The object information acquiring apparatus according to claim 12, further comprising a projection amount designator that determines a range of voxels in a projecting direction when acquiring the projection image data.

18. The object information acquiring apparatus according to claim 17, wherein the processor acquires a plurality of sets of projection image data by shifting the range of voxels determined by the projection amount designator by one voxel at a time.

19. The object information acquiring apparatus according to claim 12, wherein the processor aligns a coordinate system of the intensity-dependent three-dimensional image data and a coordinate system of the non-intensity-dependent three-dimensional image data.

20. The object information acquiring apparatus according to claim 12, wherein the intensity-dependent three-dimensional image data is data that enables an image of a measurement target to be distinguished from noise according to a value, and the non-intensity-dependent three-dimensional image data is data for which it is difficult to distinguish between an image of the measurement target and noise according to a value.

21. The object information acquiring apparatus according to claim 12, wherein
the intensity-dependent three-dimensional image data is any of a distribution of initial acoustic pressure, a distribution of a light energy absorption density, a distribution of an absorption coefficient, and B-mode image data; and
the non-intensity-dependent three-dimensional image data is a distribution of presence ratios of substances that compose the object or color Doppler image data.

22. The object information acquiring apparatus according to claim 12, further comprising a display that displays the projection image data.

23. The object information acquiring apparatus according to claim 12, wherein the projection plane is a two-dimensional plane.

24. The object information acquiring apparatus according to claim 18, wherein the processor acquires three-dimensional image data using the plurality of sets of projection image data.

25. The object information acquiring apparatus according to claim 17, wherein the processor acquires a plurality of sets of projection image data by shifting the range of voxels determined by the projection amount designator.

26. The object information acquiring apparatus according to claim 21, wherein the distribution of presence ratios of substances is a distribution of oxygen saturation.

27. The object information acquiring apparatus according to claim 12, further comprising:
a light source that irradiates the object with light, and
a receiver that receives the acoustic waves at a plurality of measurement positions,
wherein the receiver receives the acoustic wave generated from the object which is irradiated with light from the light source, and
wherein the intensity-dependent three-dimensional image data is any of a distribution of initial acoustic pressure, a distribution of a light energy absorption density, a distribution of an absorption coefficient, and
wherein the non-intensity-dependent three-dimensional image data is a distribution of presence ratios of substances that compose the object.

28. The object information acquiring apparatus according to claim 27, wherein the distribution of presence ratios of substances is a distribution of oxygen saturation.

29. An object information acquiring method, comprising:
acquiring intensity-dependent three-dimensional image data within an object, based on acoustic waves from an object;
acquiring non-intensity-dependent three-dimensional image data within the object, based on the acoustic waves;
determining voxel coordinates projected onto a projection plane based on the intensity-dependent three-dimensional image data; and
acquiring projection image data by projecting, on the projection plane, the non-intensity-dependent three-dimensional image data corresponding to the voxel coordinates, wherein at least one of said steps is performed using a CPU.

30. A display controlling method, comprising:

displaying intensity-dependent three-dimensional image data acquired based on acoustic waves generated from an object;

selecting voxel coordinates projected onto a projection plane from among the intensity-dependent three-dimensional image data;

displaying non-intensity-dependent three-dimensional image data within the object; and displaying projection image data by projecting, on the projection plane, non-intensity-dependent three-dimensional image data, acquired based on the acoustic wave, corresponding to the voxel coordinates, wherein at least one of said steps is performed using a CPU.

31. A non-transitory computer-readable storage medium storing a program for causing a computer to perform the steps of:

acquiring intensity-dependent three-dimensional image data within an object, based on acoustic waves generated from an object, acquiring non-intensity-dependent three-dimensional image data within the object, based on the acoustic waves, determining voxel coordinates projected onto a projection plane based on the intensity-dependent three-dimensional image data, and acquiring the projection image data by projecting, on the projection plane, the non-intensity-dependent three-dimensional image data corresponding to the voxel coordinates.

32. A non-transitory computer-readable storage medium storing a program for causing a computer to perform the steps of:

displaying intensity-dependent three-dimensional image data acquired based on acoustic waves generated from an object, selecting voxel coordinates projected onto a projection plane from among the intensity-dependent three-dimensional image data, displaying non-intensity-dependent three-dimensional image data within the object, displaying projection image data by projecting, on the projection plane, non-intensity-dependent three-dimensional image data, acquired based on the acoustic wave, corresponding to the voxel coordinates.

* * * * *